United States Patent
Gunday et al.

(10) Patent No.: US 9,737,195 B2
(45) Date of Patent: Aug. 22, 2017

(54) HANDHELD RESECTOR BALLOON SYSTEM

(71) Applicants: Erhan H. Gunday, Great Neck, NY (US); Lawrence J. Gerrans, San Anselmo, CA (US); Alex Hsia, San Jose, CA (US); Devin J S Scheifele, San Mateo, CA (US); Jessie Tung, Cerritos, CA (US)

(72) Inventors: Erhan H. Gunday, Great Neck, NY (US); Lawrence J. Gerrans, San Anselmo, CA (US); Alex Hsia, San Jose, CA (US); Devin J S Scheifele, San Mateo, CA (US); Jessie Tung, Cerritos, CA (US)

(73) Assignee: Sanovas, Inc., Sausalito, CA (US)

( * ) Notice: Subject to any disclaimer, the term of this patent is extended or adjusted under 35 U.S.C. 154(b) by 487 days.

(21) Appl. No.: 14/204,844

(22) Filed: Mar. 11, 2014

(65) Prior Publication Data

US 2014/0275770 A1   Sep. 18, 2014

Related U.S. Application Data

(63) Continuation of application No. 13/837,664, filed on Mar. 15, 2013, and a continuation of application No. 13/837,970, filed on Mar. 15, 2013.

(51) Int. Cl.
*A61B 1/00* (2006.01)
*A61B 17/32* (2006.01)
(Continued)

(52) U.S. Cl.
CPC ...... *A61B 1/00154* (2013.01); *A61B 1/00082* (2013.01); *A61B 1/04* (2013.01);
(Continued)

(58) Field of Classification Search
CPC .................... A61B 17/320725; A61B 1/00082
See application file for complete search history.

(56) References Cited

U.S. PATENT DOCUMENTS

| 4,981,470 A | 1/1991 | Bombeck, IV |
| 5,007,898 A | 4/1991 | Rosenbluth et al. |

(Continued)

FOREIGN PATENT DOCUMENTS

WO   2012091364 A2   7/2012

OTHER PUBLICATIONS

International Search Report and Written Opinion of the International Searching Authority Application No. PCT/2014/024302 Completed: Aug. 29, 2014; Mailing Date: Sep. 16, 2014 11 pages.
(Continued)

*Primary Examiner* — David Bates
(74) *Attorney, Agent, or Firm* — St. Onge Steward Johnston & Reens LLC

(57) ABSTRACT

A handheld resector balloon system includes a balloon catheter with a resecting surface and hub coupled to a handheld pump. The hub includes an inflation port that supplies fluid to a first lumen of the catheter to repeatedly inflate and deflate the balloon in pulsed fashion to resect biological material. The hub may also include a delivery port for delivering an agent, such as drugs, to a second lumen of the catheter for delivery to the distal end of the catheter. The hub may also include an aperture for inserting a device, such as an imaging device, into the second lumen of the catheter. In some embodiments, an imaging module is coupled to a handheld pump, which may include a light source for supplying light, and image circuitry for converting an optical signal from the imaging device to electrical data to be output to a computer.

29 Claims, 19 Drawing Sheets

(51) Int. Cl.

| | |
|---|---|
| A61B 1/06 | (2006.01) |
| A61B 1/04 | (2006.01) |
| A61B 1/07 | (2006.01) |
| A61B 1/12 | (2006.01) |
| A61B 17/12 | (2006.01) |
| A61B 17/3205 | (2006.01) |
| A61B 17/3207 | (2006.01) |
| A61B 90/57 | (2016.01) |
| A61B 90/30 | (2016.01) |
| A61M 25/10 | (2013.01) |
| A61B 17/24 | (2006.01) |
| A61B 17/22 | (2006.01) |
| A61B 17/00 | (2006.01) |
| A61B 90/00 | (2016.01) |

(52) U.S. Cl.
CPC .......... *A61B 1/0669* (2013.01); *A61B 1/0684* (2013.01); *A61B 1/07* (2013.01); *A61B 1/128* (2013.01); *A61B 17/12136* (2013.01); *A61B 17/3205* (2013.01); *A61B 17/320725* (2013.01); *A61B 90/30* (2016.02); *A61B 90/57* (2016.02); *A61B 1/00087* (2013.01); *A61B 1/00165* (2013.01); *A61B 17/24* (2013.01); *A61B 2017/00544* (2013.01); *A61B 2017/22061* (2013.01); *A61B 2090/0807* (2016.02); *A61B 2090/306* (2016.02); *A61B 2090/309* (2016.02); *A61M 25/10181* (2013.11)

(56) References Cited

U.S. PATENT DOCUMENTS

| | | |
|---|---|---|
| 5,090,959 A | 2/1992 | Samson et al. |
| 5,316,016 A | 5/1994 | Adams et al. |
| 5,537,304 A | 7/1996 | Klaus |
| 5,749,848 A | 5/1998 | Jang et al. |
| 5,967,984 A | 10/1999 | Chu et al. |
| 6,023,542 A | 2/2000 | Pan et al. |
| 6,045,240 A | 4/2000 | Hochstein |
| 6,084,354 A | 7/2000 | Kohmura et al. |
| 6,102,929 A | 8/2000 | Conway et al. |
| 6,787,999 B2 | 9/2004 | Stimac et al. |
| 7,198,397 B2 | 4/2007 | Bennett et al. |
| 7,264,624 B2 | 9/2007 | Nash et al. |
| 7,668,450 B2 | 2/2010 | Todd et al. |
| 7,736,336 B2 | 6/2010 | Plishka et al. |
| 7,871,184 B2 | 1/2011 | Peng |
| 7,874,699 B2 | 1/2011 | Liang |
| 7,914,517 B2 | 3/2011 | Baran et al. |
| 7,988,633 B2 | 8/2011 | Hossack et al. |
| 8,070,329 B1 | 12/2011 | Bechtel et al. |
| 8,172,834 B2 | 5/2012 | Bhadri et al. |
| 8,177,397 B1 | 5/2012 | Knoble et al. |
| 8,206,015 B2 | 6/2012 | Cho et al. |
| 8,206,374 B2 | 6/2012 | Duane et al. |
| 8,226,601 B2 | 7/2012 | Gunday et al. |
| 8,242,669 B2 | 8/2012 | Qiu |
| 8,246,230 B2 | 8/2012 | Todd et al. |
| 8,258,682 B2 | 9/2012 | Villard |
| 8,272,762 B2 | 9/2012 | Maxik et al. |
| 8,299,693 B2 | 10/2012 | Chen |
| 8,419,225 B2 | 4/2013 | Zeng et al. |
| 8,419,240 B2 | 4/2013 | Lim |
| 8,427,059 B2 | 4/2013 | Betsuda et al. |
| 8,430,533 B1 | 4/2013 | Blalock et al. |
| 8,434,917 B2 | 5/2013 | Lai |
| 8,449,169 B2 | 5/2013 | Maslowski et al. |
| 8,474,999 B2 | 7/2013 | Ou et al. |
| 8,492,961 B2 | 7/2013 | Zeng |
| 8,500,316 B2 | 8/2013 | Hisayasu et al. |
| 8,517,576 B2 | 8/2013 | Yang et al. |
| 8,562,181 B2 | 10/2013 | Dong et al. |
| 8,579,471 B2 | 11/2013 | Boomgaarden et al. |
| 8,585,249 B2 | 11/2013 | Huang |
| 8,591,069 B2 | 11/2013 | Horn |
| 8,602,597 B2 | 12/2013 | Lopez et al. |
| 8,608,341 B2 | 12/2013 | Boomgaarden et al. |
| 8,646,942 B2 | 2/2014 | Boomgaarden et al. |
| 8,651,705 B2 | 2/2014 | Wilcox et al. |
| 8,680,755 B2 | 3/2014 | Lim et al. |
| 8,684,563 B2 | 4/2014 | Lin et al. |
| 8,686,623 B2 | 4/2014 | Wheelock et al. |
| 8,686,641 B2 | 4/2014 | Maxik et al. |
| 8,696,170 B2 | 4/2014 | Huang |
| 2002/0077593 A1 | 6/2002 | Perkins et al. |
| 2003/0214810 A1 | 11/2003 | Zhang |
| 2004/0230116 A1 | 11/2004 | Cowan et al. |
| 2005/0007783 A1 | 1/2005 | Ono |
| 2005/0041428 A1 | 2/2005 | Zhang |
| 2005/0158687 A1 | 7/2005 | Dahm |
| 2006/0061997 A1 | 3/2006 | Lin |
| 2006/0274529 A1 | 12/2006 | Cao |
| 2006/0282153 A1 | 12/2006 | Jang |
| 2007/0133209 A1 | 6/2007 | Wang et al. |
| 2007/0211470 A1 | 9/2007 | Huang |
| 2007/0230186 A1 | 10/2007 | Chien |
| 2007/0236935 A1 | 10/2007 | Wang |
| 2007/0253202 A1 | 11/2007 | Wu et al. |
| 2007/0285926 A1 | 12/2007 | Maxik |
| 2008/0077085 A1 | 3/2008 | Eidenschink et al. |
| 2008/0161890 A1 | 7/2008 | Lafontaine |
| 2008/0212325 A1 | 9/2008 | Wang |
| 2008/0253125 A1 | 10/2008 | Kang et al. |
| 2008/0266866 A1 | 10/2008 | Tsai |
| 2008/0291401 A1 | 11/2008 | Lo et al. |
| 2009/0002995 A1 | 1/2009 | Lee et al. |
| 2009/0009999 A1 | 1/2009 | Wang et al. |
| 2009/0021944 A1 | 1/2009 | Lee et al. |
| 2009/0034261 A1 | 2/2009 | Grove |
| 2009/0046464 A1 | 2/2009 | Liu et al. |
| 2009/0046465 A1 | 2/2009 | Hashimoto et al. |
| 2009/0141500 A1 | 6/2009 | Peng |
| 2009/0147520 A1 | 6/2009 | Liu et al. |
| 2009/0153797 A1 | 6/2009 | Allon et al. |
| 2009/0154166 A1 | 6/2009 | Zhang et al. |
| 2009/0175041 A1 | 7/2009 | Yuen et al. |
| 2009/0192494 A1 | 7/2009 | Michishita et al. |
| 2009/0264866 A1 | 10/2009 | Powell |
| 2009/0284155 A1 | 11/2009 | Reed et al. |
| 2009/0290382 A1 | 11/2009 | Liao |
| 2009/0296402 A1 | 12/2009 | Chang et al. |
| 2010/0110691 A1 | 5/2010 | Hsu et al. |
| 2010/0121270 A1 | 5/2010 | Gunday et al. |
| 2010/0149818 A1 | 6/2010 | Ruffin |
| 2010/0195329 A1 | 8/2010 | Inoue et al. |
| 2010/0232164 A1 | 9/2010 | Tessnow et al. |
| 2010/0296272 A1 | 11/2010 | Roos et al. |
| 2011/0044039 A1 | 2/2011 | Chung et al. |
| 2011/0044049 A1 | 2/2011 | Boyer |
| 2011/0044050 A1 | 2/2011 | Chiu |
| 2011/0057552 A1 | 3/2011 | Weaver |
| 2011/0128730 A1 | 6/2011 | Chiu |
| 2011/0152683 A1 | 6/2011 | Gerrans et al. |
| 2011/0164420 A1 | 7/2011 | Lee |
| 2011/0222291 A1 | 9/2011 | Peng |
| 2011/0260647 A1 | 10/2011 | Catalano et al. |
| 2012/0081904 A1 | 4/2012 | Horng |
| 2012/0120635 A1 | 5/2012 | Strong et al. |
| 2012/0140462 A1 | 6/2012 | Pickard |
| 2012/0140465 A1 | 6/2012 | Rowlette, Jr. et al. |
| 2012/0155059 A1 | 6/2012 | Hoelen et al. |
| 2012/0162994 A1 | 6/2012 | Wasniewski et al. |
| 2012/0238816 A1 | 9/2012 | Gunday et al. |
| 2012/0241781 A1 | 9/2012 | Yuan et al. |
| 2012/0259217 A1 | 10/2012 | Gerrans et al. |
| 2012/0291259 A1 | 11/2012 | Popovich et al. |
| 2013/0100674 A1 | 4/2013 | Kim et al. |
| 2013/0223061 A1 | 8/2013 | Hwu et al. |
| 2013/0258672 A1 | 10/2013 | Bell |

(56) References Cited

U.S. PATENT DOCUMENTS

2013/0294085 A1 11/2013 Watanabe et al.
2013/0301275 A1 11/2013 Kim

OTHER PUBLICATIONS

International Search Report and Written Opinion of the International Searching Authority Application No. PCT/US2014/018948 Completed: Nov. 14, 2014; Mailing Date: Dec. 8, 2014 7 pages.
International Search Report and Written Opinion of the International Searching Authority Application No. PCT/US2014/017539 Completed: May 19, 2014; Mailing Date: Jun. 13, 2014 9 pages.

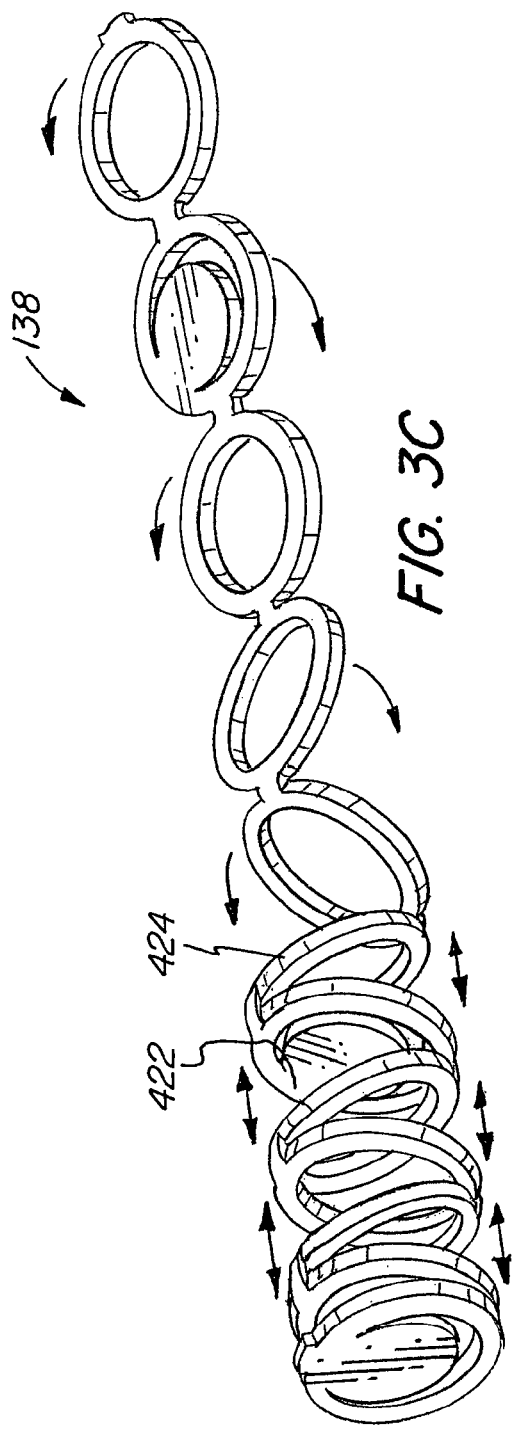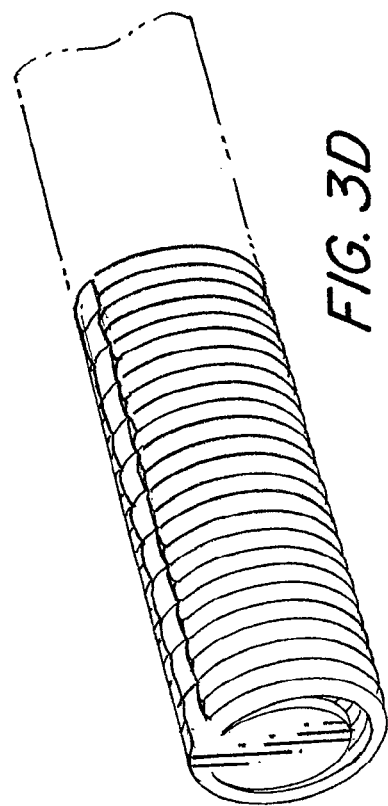

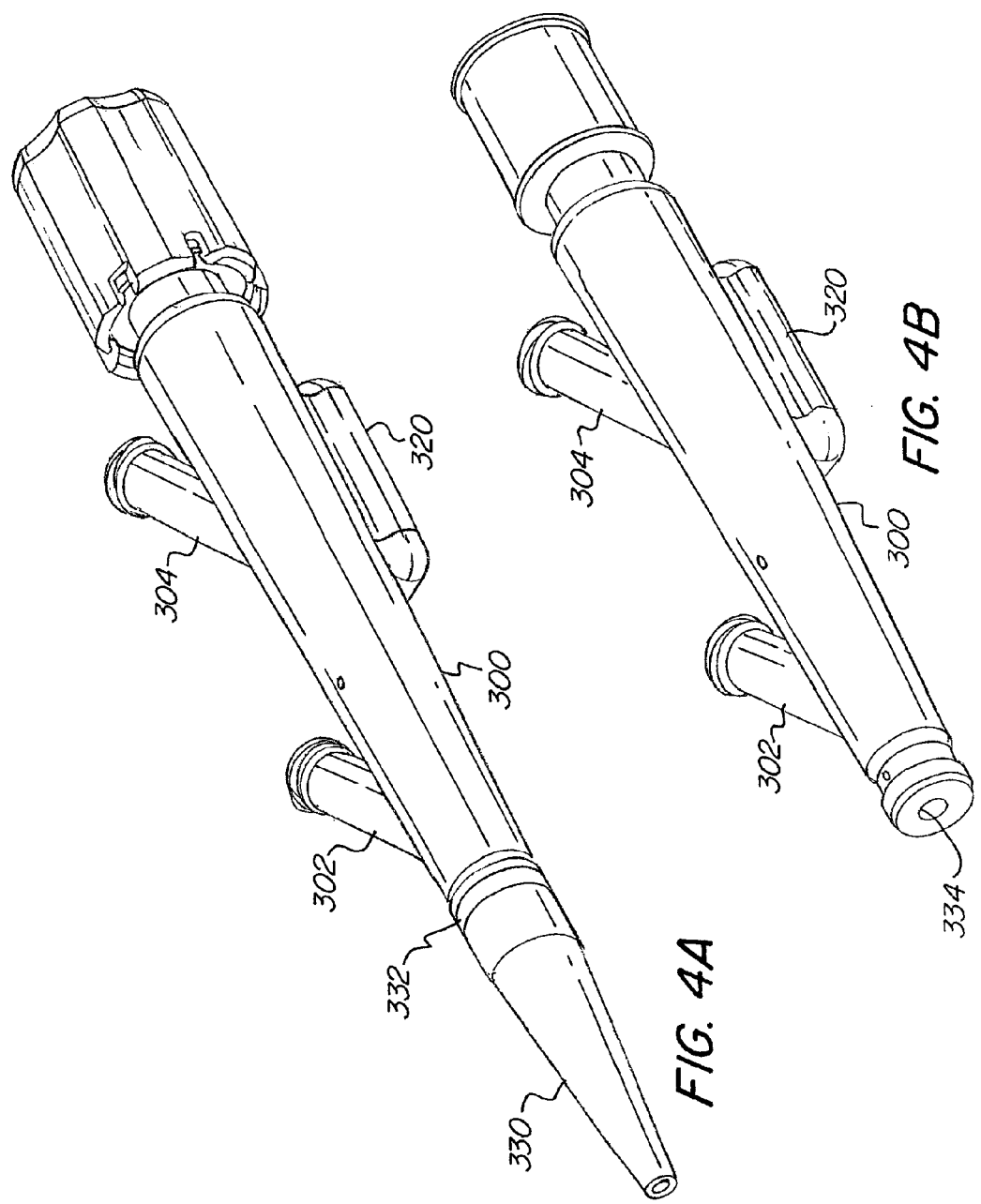

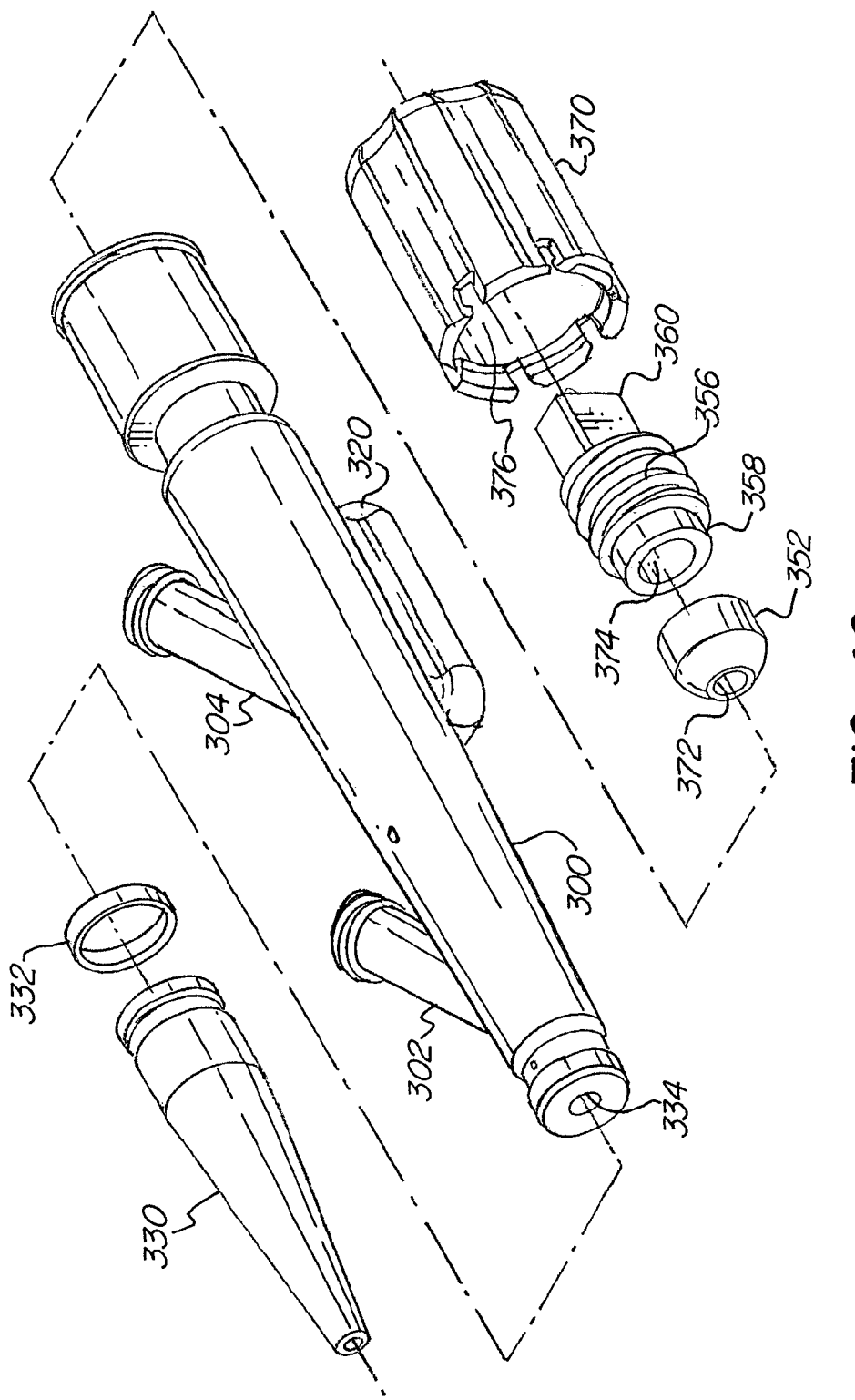

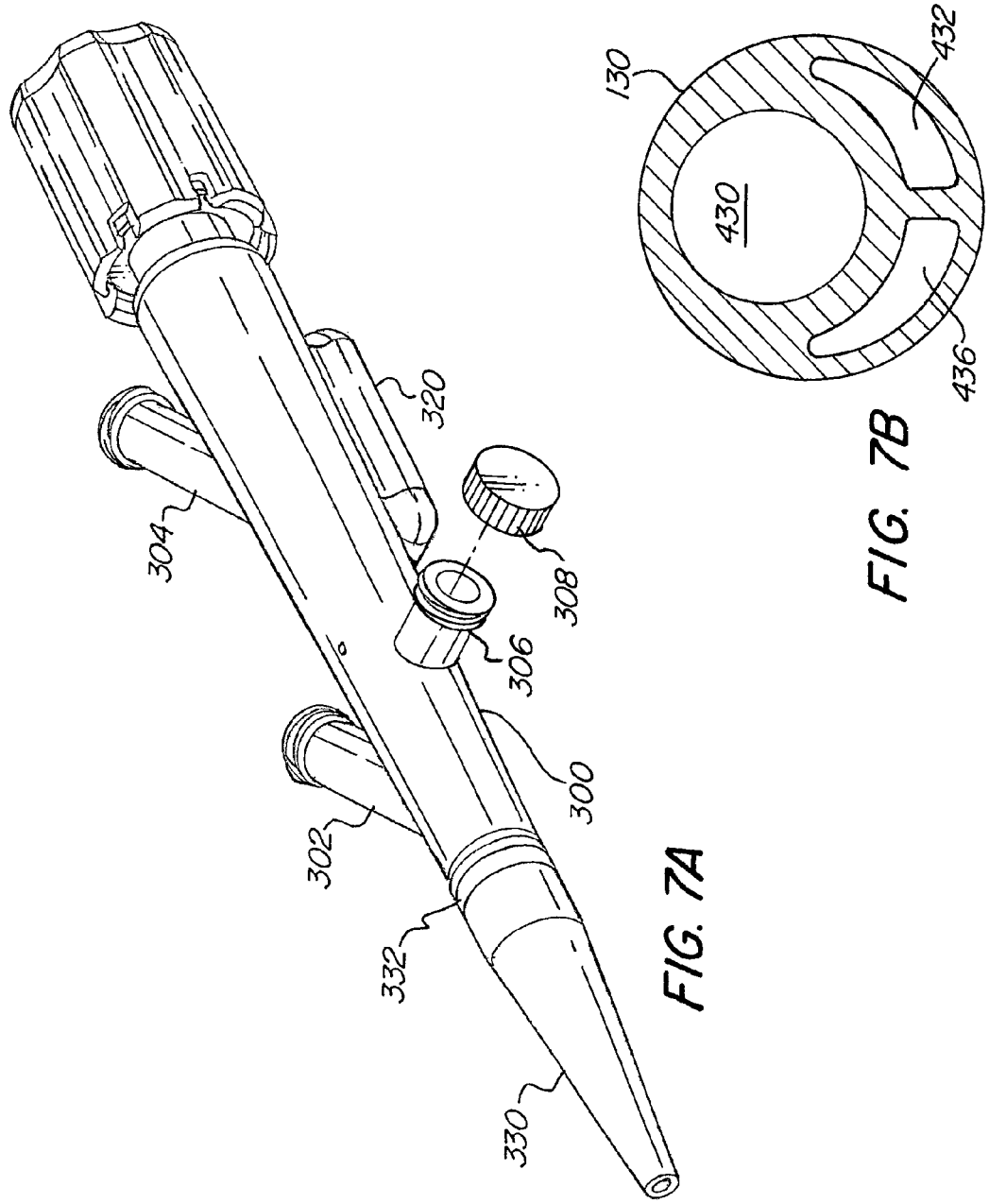

HANDHELD RESECTOR BALLOON SYSTEM

FIELD OF THE INVENTION

The present invention relates to devices for the resection of unwanted biological material, such as tissue growths and tumors, in bodily cavities. More specifically, the invention relates to a balloon catheter with a resecting surface that is inflated with a handheld device to resect the target material with minimal trauma.

BACKGROUND OF THE INVENTION

The removal of unwanted and/or life threatening biological material from interior portions of bodily cavities, such as organs, vessels, articular joints and structures, sinuses, and various bodily lumens, is a very common procedure in various medical specialties and disciplines, such as pulmonology, cardiology, urology, gynecology, gastro-enterology, neurology, otolaryngology, orthopedics, and general surgery. Accordingly, various instruments and methods have been employed to perform these procedures, which are generally well known in the art.

One of the most important complications in such procedures is bleeding. The bleeding and resulting morbidity of tissue that occurs in many of the currently known surgical procedures is the result of abrasive, traumatic, and invasive excising and removal techniques. Many of these techniques risk perforation of the vessel or lumen in which the procedure is being performed, resulting in grave complications for the surgeon and patient. In addition, many patient maladies are simply not remedied by these procedures because no interventional, minimally invasive treatment modality exists, the methods are not efficient, safe, and reproducible, and/or the instruments employed lack the appropriate visualization, physiological measurement, and/or feedback necessary to ensure the safety, efficacy, and reproducibility of the procedure. Accordingly, a new type of treatment is required.

One instrument that is commonly used in various types of medical procedures is an inflatable balloon catheter, of which many different types exist, which are utilized to perform various necessary functions. For example, these inflatable balloons are often used to control or stop bleeding, to hold instruments in place, or to prevent or facilitate other flow or movement within the bodily cavity. For example, many urological catheters are held in place via a balloon that impacts the sidewalls of the urinary tract, many gynecological instruments are held in place via balloons that impact the sidewalls of the vaginal vault, endovascular balloons are often used to control bleeding, inflatable balloons are sometimes used to control the backflow of radio-opaque agents injected into the cystic duct to detect the presence of gall stones during general surgical cholecystectomy procedures, and, recently, balloon catheters have been employed to release sinus congestion.

One particular application of such catheters is lung cancer. Among all types of cancer, this has the lowest survival rate, as more than one third of all deaths due to cancer are caused by lung cancer. Over 1.5 million new cases are diagnosed worldwide each year. The most frequent cause of death for lung cancer patients is airway obstruction. In lung cancer patients, one third of all cases initially, and another third of the cases in the long term, present main airway obstruction, which may cause asphyxia, hemorrhaging, and infection. These complications are the most frequent causes of death in lung cancer patients.

Use of interventional bronchoscopy for the treatment of lung cancer and the resultant airway obstruction increases the quality of life and survival rates of patients suffering from Chronic Obstructive Pulmonary Disease (COPD) and the obstructive co-morbidities associated with the cancer. Accordingly, balloon catheters have been routinely used with various endoscopes and with flexible and rigid bronchoscopes for dilation, as a tamponade to stop bleeding, and as an interference fixation device to hold instruments in place and prevent the retropulsion of those instruments under backflow pressure.

In light of the aforementioned need for a new type of treatment for removing undesirable biological material in bodily cavities, it has been realized that inflatable balloon catheters may further be employed as interventional tools for the excision and removal of such materials—such as endoluminal obstructions and tumors and endovascular occlusions—in various applications, such as the aforementioned interventional medical specialties of pulmonology, cardiology, urology, gynecology, gastro-enterology, neurology, otolaryngology, and general surgery. The use of balloon catheters in this way has presented a method of treatment that is simple, safe, highly effective, and inexpensive compared to other types of methods and devices that are used, such as mechanical, laser, electrocautery, cryotherapy, etc.

Accordingly, a new class of balloons has been suggested for this purpose, such as that disclosed in U.S. Pat. No. 8,226,601 to Gunday et al., the specification of which is hereby incorporated by reference herein in its entirety. This device employs a balloon catheter with an inflatable resector balloon. Using this device, one is able to treat obstruction in a bodily cavity by inserting the catheter with the balloon deflated into the bodily cavity. The balloon is aligned with the obstruction and then repeatedly inflated and deflated in pulsed fashion. The balloon's abrasive surface, when gradually pulsed in this way, gradually and non-traumatically resects the obstruction, while causing minimal damage to the surrounding, healthy tissue.

While this system is of great use for safely removing undesirable biological materials from bodily cavities, there is a need to also provide a system that does not rely on separate control units to operate the resection system. For example, prior systems may employ an electro-pneumatic pump, which is very accurate and convenient. However, such a device may need to be mounted on a rack or boom arm with other self-contained units, such as camera control units, insufflators, and electrosurgical units, not within the surgeon's reach, such that the surgeon will need to move away from the operating table or rely on assistants in order to make adjustments. Moreover, many medical practitioners prefer to be able to directly and actively control the operation of the devices they are using to perform the procedure, rather than relying on a device to control them automatically based on previously entered parameters.

In addition, the resector balloon catheter must be inserted into a narrow and vital body cavity, such as a respiratory airway or coronary artery, and the doctor must conduct a precise procedure using the inserted device. Accordingly, it is desirable to have imaging available to provide the doctors with a view that facilitates precise positioning and operation of the device. Such imaging systems typically comprise some kind of manually manipulated scope, connected to a camera control unit for receiving and processing the optical signals that, as referenced above, is typically a self-contained unit located on a rack or boom arm. A separate imaging system such as this can be difficult to hold and manipulate while one is also holding and operating a handheld balloon catheter and pump.

Also, the interior of the human body is almost completely dark, and proper illumination of the target site inside the body is required in order to obtain useful images. Specifically, light must be delivered to the interior body, into the field of view of the imaging device, such that the reflected light can be captured and transmitted to an appropriate device for rendering those images.

In traditional operating environments, light is transmitted from an external light source into the patient. Since these light sources must be very bright in order to provide sufficient illumination for imaging, they tend to generate significant heat. Since they generate so much heat, which could damage any biological tissue with which they come into contact, it is common to use self-contained, external light sources. A typical example of this is described in U.S. Pat. Nos. 7,668,450 and 8,246,230 to Todd et al. As described therein, a typical light source unit includes a light bulb, a ballast power supply, controls, and cooling fans. These light source units are, like the electro-pneumatic pump and camera control unit discussed above, typically mounted on a rack or boom arm along with other devices. The light generated by this light source in supplied through a light guide, such as a fiber optic cable, which transmits the light to the instrument being used in the patient.

These light sources, which require a lot of space and power, have a number of disadvantages. First, they are inefficient, as they must generate extremely intense light in order to compensate for the distance the light must travel along the cable from the unit to the instrument. Additionally, they can create dangerous conditions by transmitting heat energy to the patient. Further, the light cable is both cumbersome and further adds to the hazard of having too many cables in an already crowded room that can trip the medical professional or supporting personnel.

Accordingly, it has been proposed to instead use LEDs as a source of illumination. Because they are so small, they can be integrated into the imaging device, much closer to the target site, and their high light output, low cost, longevity, and reliability make them a desirable solution.

However, LED based light sources can get very hot during operation, and thus, can cause burns and equipment damage due to these high operating temperatures. These problems are very prominent when the light source is integrated in a portable or handheld medical device, which the LED will heat up. This can be hazardous for the patient, who will be in direct contact with the hot imaging device or instrument housing the LED, or possibly the hot LED itself, which can result in burns. Likewise, the medical practitioner holding the medical device can likewise be burned, resulting in injury to the practitioner, as well as serious injury to the patient if the practitioner unexpectedly moves or drops the instrument as a result. Additionally, heat can damage the device housing the LED, such as the optical elements of the imaging device.

Moreover, in addition to facilitating insertion of an imaging device, fluid must be continually supplied and withdrawn from the resecting balloon in order for it to function, and it is also desirable to deliver diagnostic and/or therapeutic agents to the target site to help diagnose and treat the pathology. All of these features, of course, add to the complexity of the resection system. In order to accommodate them, the catheter must have multiple lumens. Furthermore, the catheter must remain as slim as possible to be able to enter narrow passages in the body. Finally, all of these devices and components (i.e., optics, pressurized fluid for the balloon, drugs) must be fed into the various lumens of the catheter from outside of the patient's body.

What is desired, therefore, is a resector balloon system for removing undesirable biological materials that repeatedly inflates and deflates the balloon in pulsed fashion to resect the biological material that a medical practitioner can hold and actively control while performing the procedure. What is also desired is a resector balloon system that is able to facilitate precise positioning and operation of that device. What is further desired is an assembly that is able to facilitate diagnosis and/or additional treatment steps during the resection procedure with a small and efficient assembly.

SUMMARY OF THE INVENTION

Accordingly, it is an object of the present invention to provide a resector balloon system that allows a user to manually control actuation of the pump for inflating the balloon.

It is another object of the present invention to provide a resector balloon system that also provides illumination and imaging of the target site that is not difficult to hold and manipulate while operating the pump.

It is a further object of the present invention to provide a resector balloon system that can efficiently deliver other fluids in addition to the balloon inflation air, such as diagnostic and/or therapeutic agents, to the target site.

It is yet another object of the present invention to provide a resector balloon catheter that achieves the delivery of additional fluids and devices while maintaining simplicity and compactness.

Accordingly, the invention comprises a handheld resector balloon system that overcomes the deficiencies of the prior art and achieves at least some of the objects and advantages listed.

BRIEF DESCRIPTION OF THE DRAWINGS

FIGS. 3B-D are isometric views of the cleaning member of the catheter in the assembly of FIGS. 2A-B.

FIG. 4A is an isometric view of the hub in the assembly of FIGS. 2A-B.

FIG. 4B is an isometric view of the hub of FIG. 4A without a strain relief or sealing mechanism.

FIG. 4C is an exploded view of the hub of FIG. 4A.

FIG. 7A is an isometric view of a hub for use in the assembly of FIGS. 2A-B.

FIG. 7B is a cross-sectional view of a catheter for use with the hub of FIG. 7A.

DETAILED DESCRIPTION OF THE INVENTION

Figure 1:
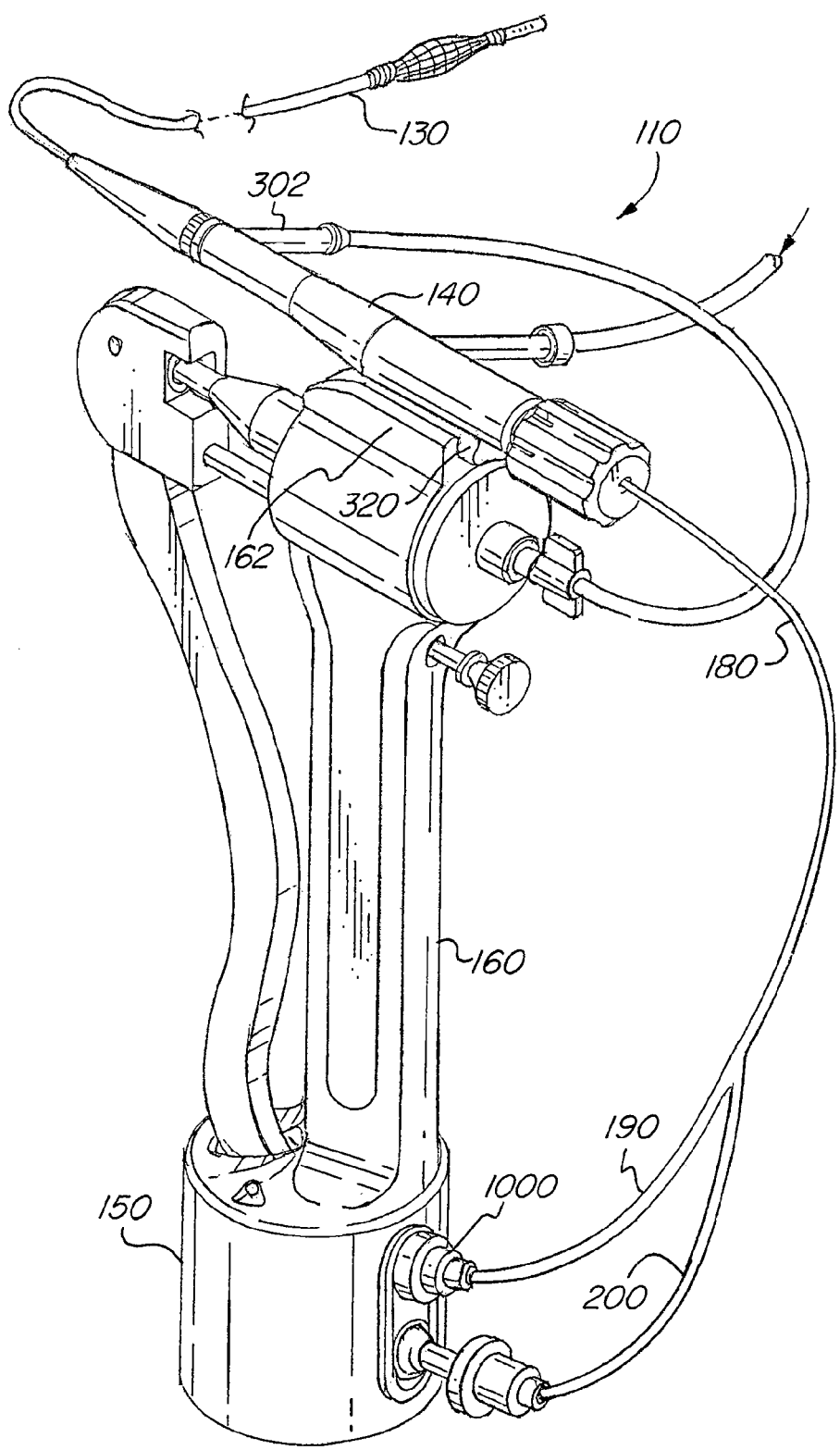
FIG. 1 is an isometric view of a handheld resector balloon system in accordance with the invention.

The basic components of one embodiment of a resector balloon system in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

FIG. 1 is an isometric view of a handheld medical device 110 in accordance with the present invention. Medical device 110 includes a handheld pump 160. A resector balloon catheter 130 and hub 140 are mounted to the top of the pump 160, and an imaging module 150 is coupled to the bottom of pump 160. An imaging device 180 is inserted into the rear of catheter hub 140, and is fed through a lumen of the hub 140 and catheter 130 and out through the distal tip of the catheter 130 in order to provide a surgeon with a view of the interior of a patient's body.

Figure 2A:
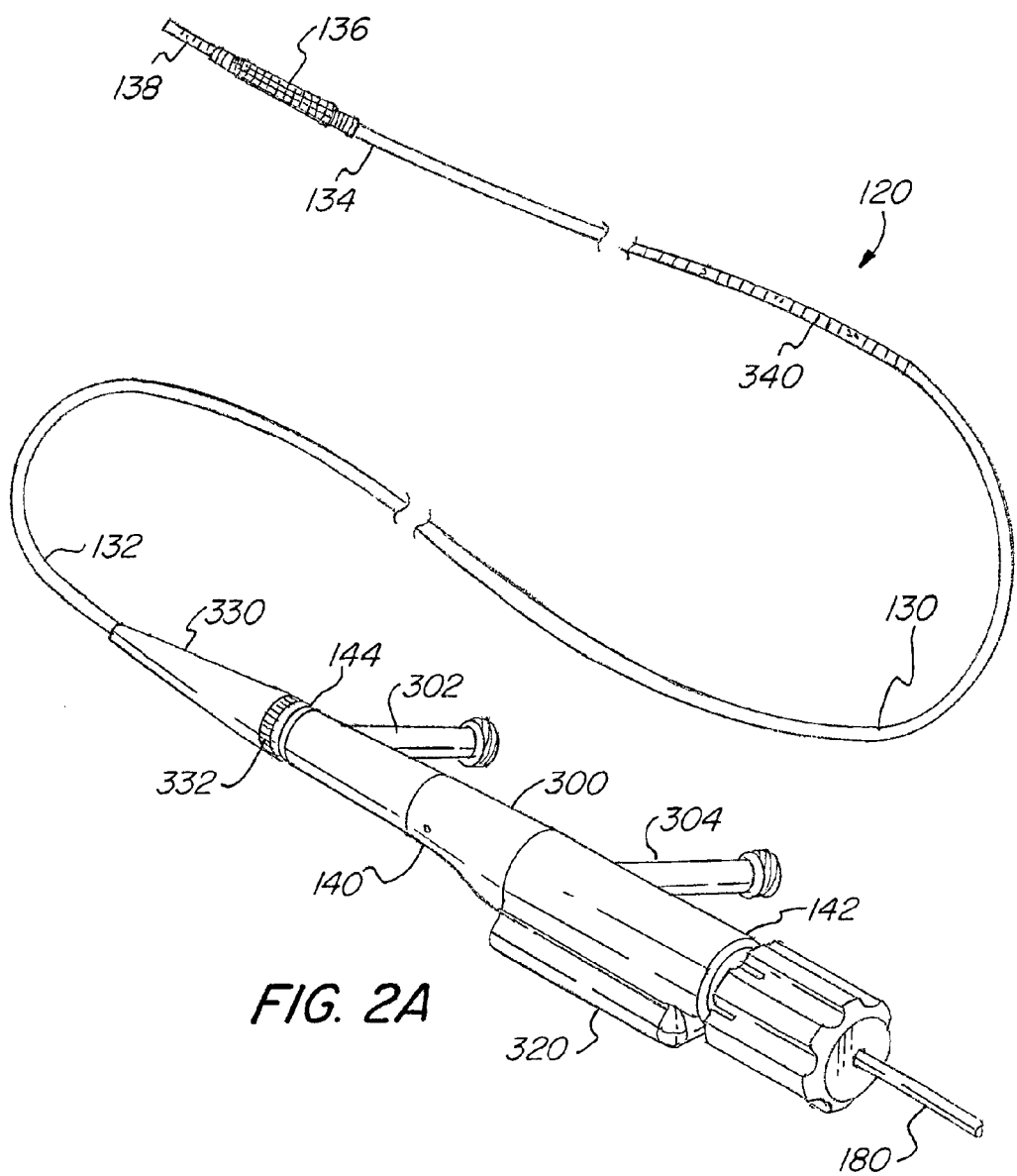
FIGS. 2A-B are isometric views of the catheter assembly of FIG. 1.
Figure 2B:
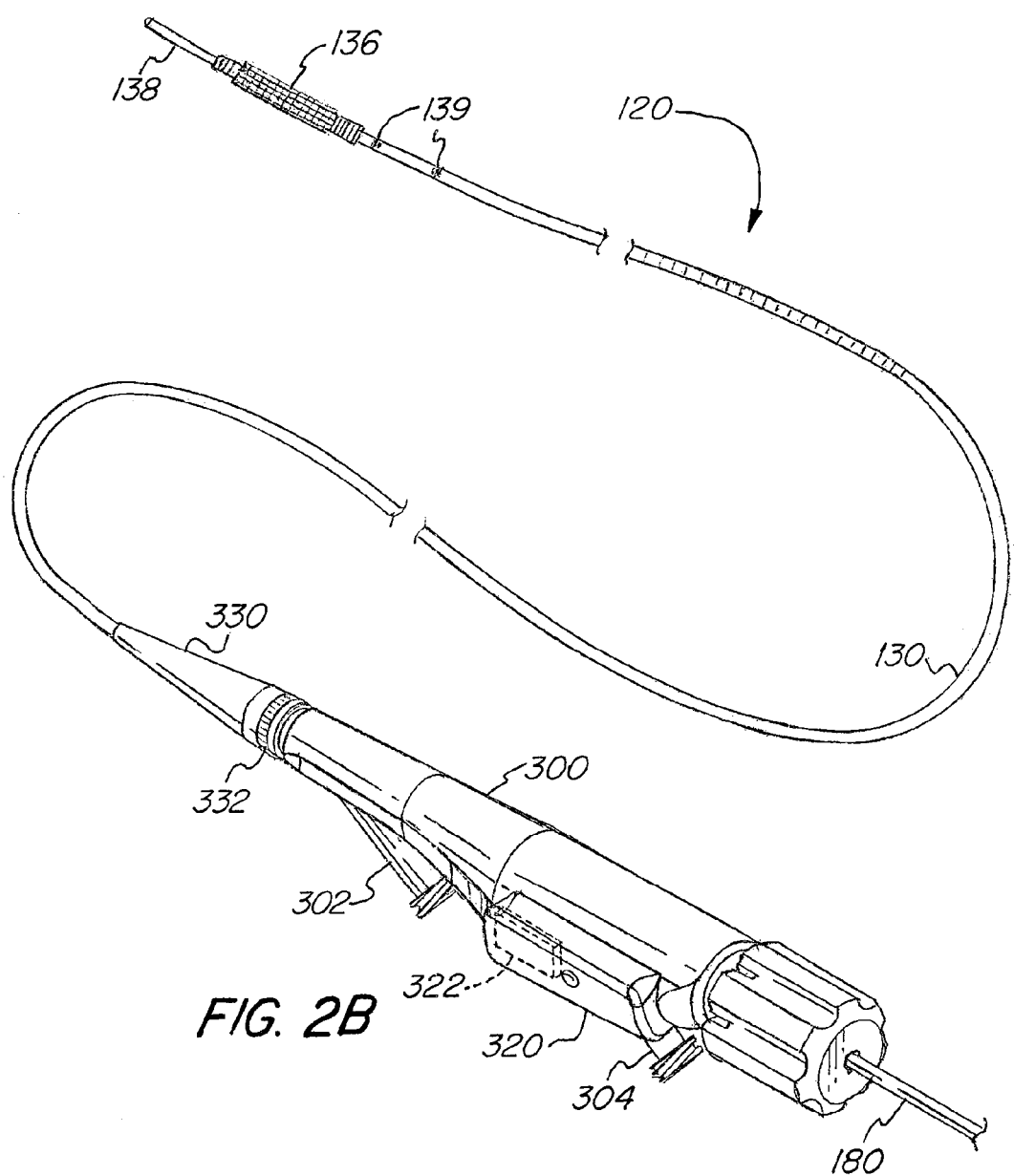

As shown in FIGS. 2A-B, the catheter assembly 120 includes hub 140 and catheter 130. The catheter 130 has a proximal portion 132 and a distal portion 134. The hub 140 includes a housing 300, which has a proximal portion 142 and a distal portion 144 to which the proximal portion 132 of the catheter 130 is coupled. The distal portion 134 of catheter 130 includes an inflatable balloon 136, which has a textured surface on the outer wall thereof for resecting biological material, as described in Gunday et al.

In certain advantageous embodiments, this resecting surface is a mesh affixed to the balloon 136. In addition to resection, the textured surface assists in precisely guiding and positioning the device by ensuring that the balloon does not slip, and also ensures more uniform expansion of balloon 136 upon inflation. The mesh may be made of elastane, latex, polyurethane, composite springs, metallic fibers, elastic, steel fibers, cotton yarn, or other appropriate material, or a composite or coating thereof. A mesh sleeve may be disposed on the outer surface of balloon 136 by using any suitable manufacturing method. Alternatively, the mesh may be knitted or woven from thread directly onto balloon 136. In other advantageous embodiments, dimensional surface structures, such as bumps or inflatable sinuses that are encapsulated in the surface substrate of the balloon 136, may be used to produce surface protrusions that form the textured surface, such as is disclosed in U.S. Published Patent Application No. 2011/0152683 by Gerrans et al.

The hub 140 includes an inflation port 302, to which hand pump 160 is coupled in order to supply fluid, such as air, to inflate the balloon 136.

The hub 140 also includes a delivery port 304, to which another source is coupled, in order to deliver a fluid to the target site. This may be a source of a diagnostic and/or therapeutic agent, such as, for example, a syringe with a pre-measured amount of a drug.

The inflation port 302 and the delivery port 304 shown in FIGS. 2A-B are integrally formed with the housing 300. Additionally, the housing 140 includes a protuberance 320 for mounting the hub 140 to an inflation device. For example, the protuberance may be engaged by a clamp 162 on the hand pump 160 shown in FIG. 1.

In certain embodiments, the protuberance 320 of the hub 140 includes an indicator 322 corresponding to a characteristic of the catheter 130 and/or balloon 136. For example, the indicator may indicate the diameter of the catheter 130, or the maximum inflation diameter, volume, or pressure of the balloon 136. This information may be computer-readable, thereby allowing another device, such as pump 160, to determine these characteristics. The indicator 322 may be, for example, an RFID tag, a 2D laser barcode, a magnetic strip, a memory device, or the like, which may be readable by the pump 160. As a result, the pump 160 or other medical equipment can use the proper settings during a medical procedure, such as a maximum pressure, so as not to allow over-inflation and popping of the balloon 136.

Figure 3A:
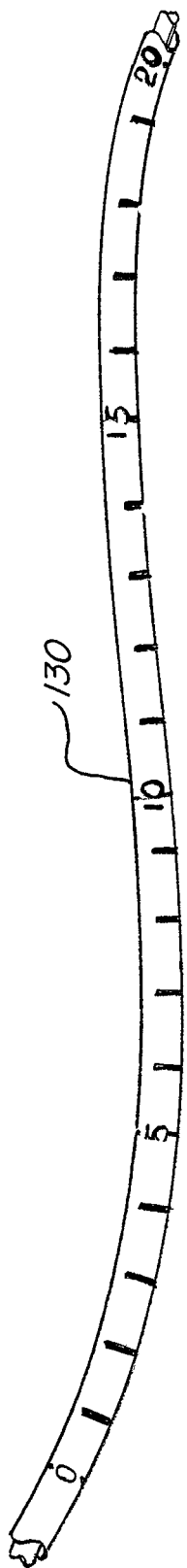
FIG. 3A is an isometric view of the catheter in the assembly of FIGS. 2A-B.

The catheter 130 includes gradation markings 340, which are also shown in greater detail in FIG. 3A. This permits the medical practitioner to more easily ascertain the depth to which the catheter 130 is inserted into a bodily cavity at any given time during a procedure. Catheter 130 also includes one or more imaging marker 139, such as radio-opaque rings, to facilitate external imaging.

A stress reliever, such as strain relief 330, is mounted to the distal end 144 of said hub 140. As shown in greater detail in FIGS. 4A-C, the strain relief 330 is placed over an aperture 334 in the housing 300 that receives the catheter 130, where there is a rigid right angle between the catheter and the surface of the housing 300 through which the aperture 334 passes. By covering the coupling of the catheter 130 to the housing 300 in this way, the strain relief 330 prevents the catheter 130 from kinking in this location during use. In some embodiments, a band 332 is affixed to the strain relief 330 and/or housing 300. The band 332 includes an indicator, such as a color, that corresponds to a characteristic of the catheter 130 and/or balloon 136, such as the diameter of the catheter 130, or the maximum inflation diameter, volume, or pressure of the balloon 136. As a result, a medical practitioner is able to quickly choose the correct balloon catheter for a given procedure.

Figure 5A:
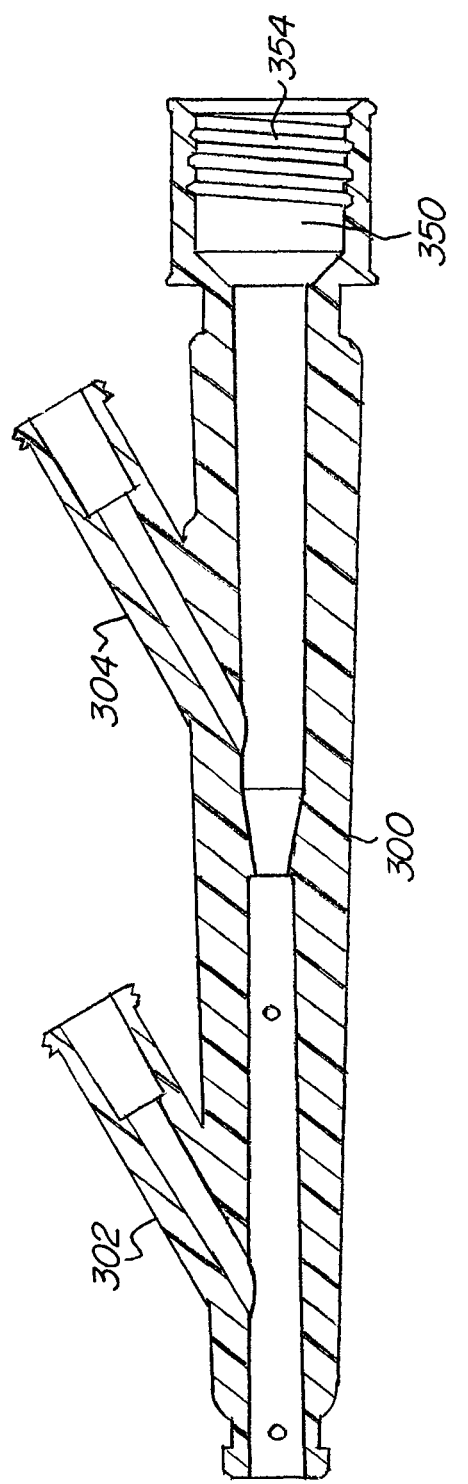
FIG. 5A is a partially cross-sectional, plan view of the hub of FIG. 4B.
Figure 5B:
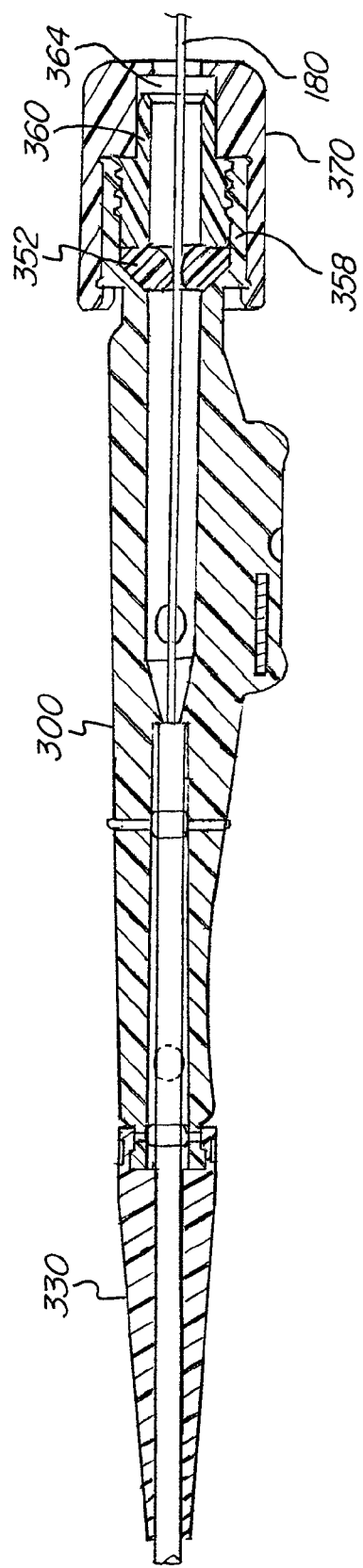
FIG. 5B is a partially cross-sectional, elevation view of the hub of FIG. 4A.

As also shown in FIGS. 4A-C, as well as FIGS. 5A-B, the proximal portion 142 of the hub 140 includes an aperture 350 for inserting a device, such as an imaging device 180, through the rear of the hub 140. A sealing member, such as a silicone plug 352, is disposed in the aperture 350 to seal in order to seal it after the imaging device 180 is inserted. The aperture 350 includes threads 354, which mate with the threads 356 of a screw 358. The screw 358 has a protrusion 360 that fits into a corresponding seat 364 of a knob 370. The plug 352, screw 358, and knob 370 each have a hole (372, 374, 376) therethrough to accommodate the imaging device 180. Once the device 180 is inserted through the holes (372, 374, 376) and into the housing 300, the knob 370 is turned, which turns the screw 358 into the threaded aperture 350. As the screw 358 presses against the plug 352, the plug 352 is compressed and deforms so as to seal the aperture 350 around the device 180. It should be noted that, although a screw 358 has been described, any driver for exerting a force of the plug 352 in order to seal the aperture 350 around the device 180 may be employed.

Figure 6A:
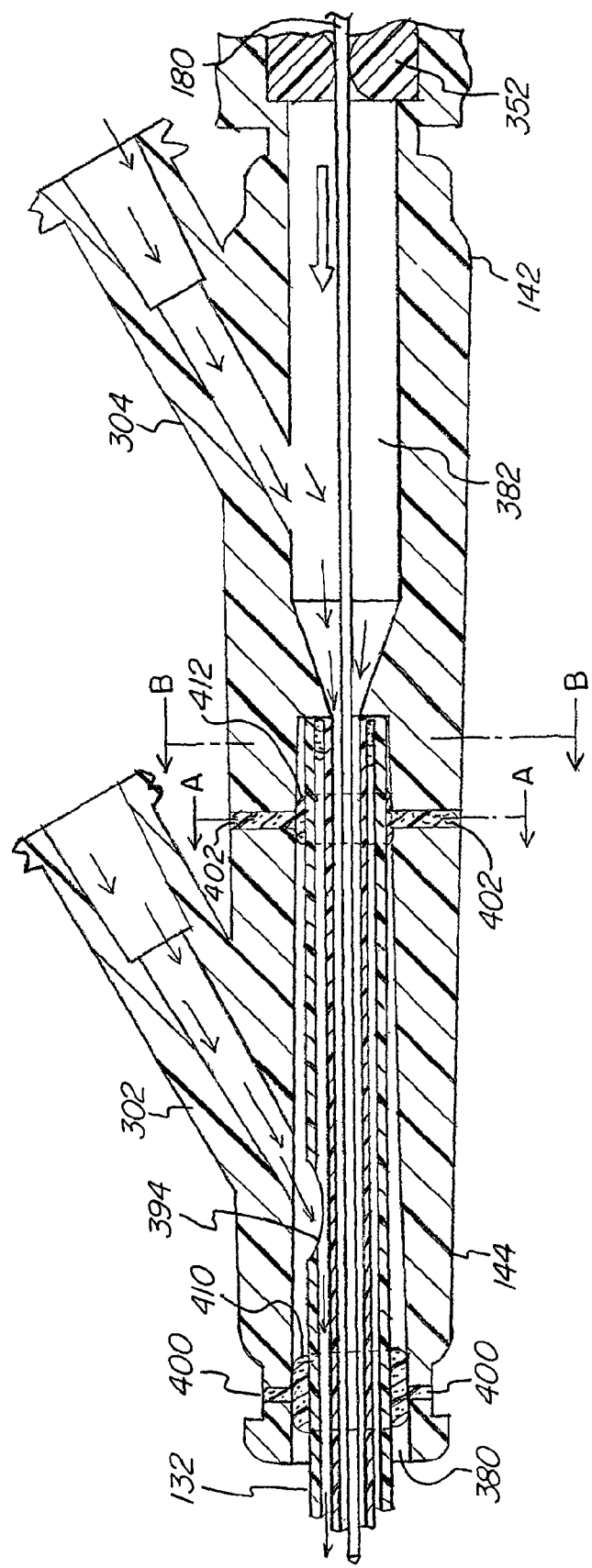
FIG. 6A is cross-sectional plan view of a portion of the hub of FIG. 4B.
Figure 6B:
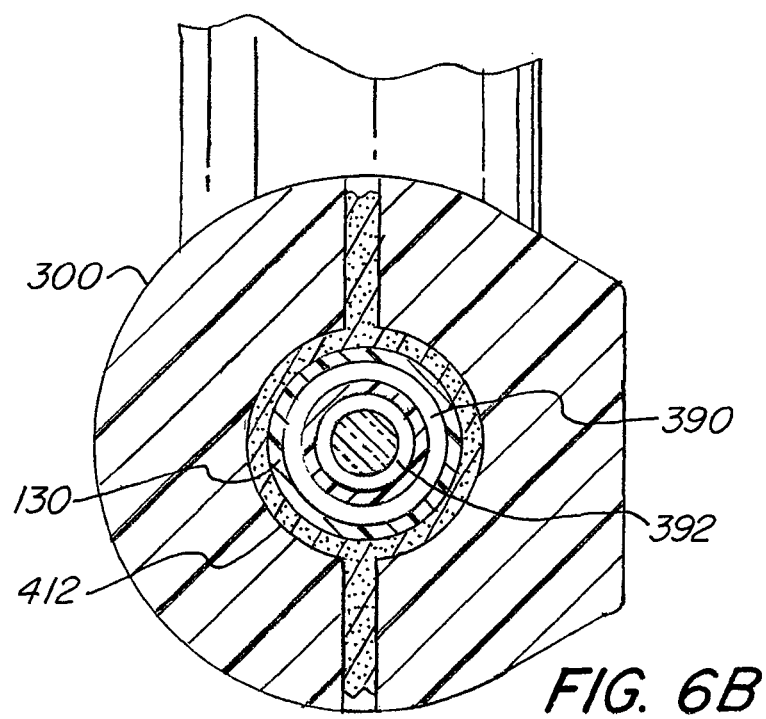
FIG. 6B is a cross-sectional view of the hub of FIG. 6A taken along line A-A.
Figure 6C:
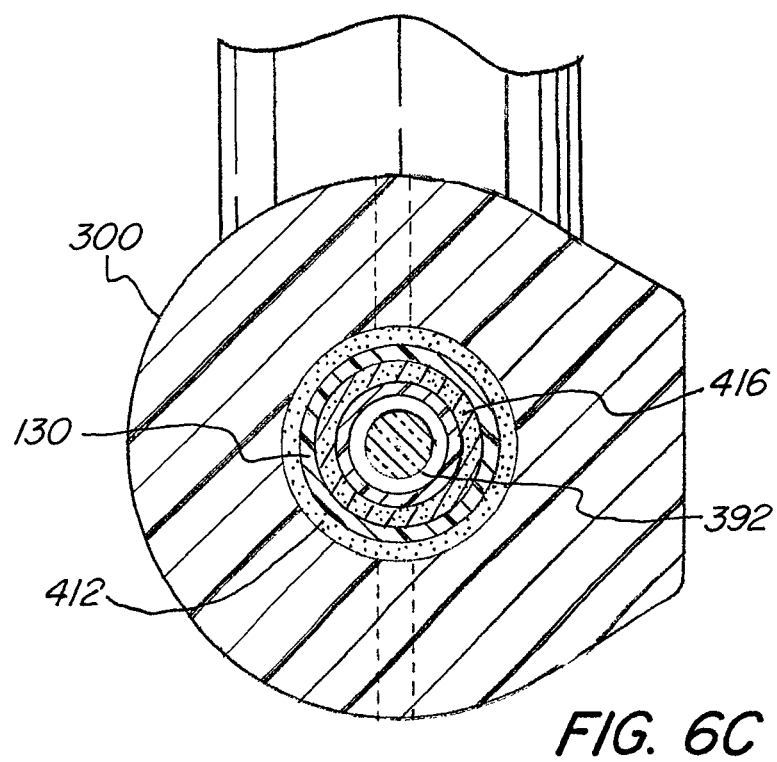
FIG. 6C is a cross-sectional view of the hub of FIG. 6A taken along line B-B.

As shown in FIGS. 6A-C, the proximal end 132 of catheter (130) is disposed in a channel 380 in the distal end 144 of the hub housing 300. The catheter 130 includes an outer lumen 390, which is in fluid communication with the interior of balloon 136, and an inner lumen 392 that also extends to the distal end of the catheter 130. The catheter 130 includes an aperture 394 that opens into the outer lumen 390, such that the inflation port 302 is in fluid communication with the outer lumen 390 and the inflation chamber of the balloon 136. As a result, a fluid source, such as pump 160, can supply fluid, such as air, to the balloon 136 to inflate it.

In order to channel the inflation air to the outer lumen 390 at a desired pressure, the housing 300 includes glue holes for providing a seal between the wall of the hub channel 380 and the catheter 130. Specifically, the housing includes glue holes 400 located distally of the inflation port 302, and glue holes 402 located proximally of the inflation port 302, for injecting glue between the wall of the hub channel 380 and the catheter 130. This produces a glue seal 410 distal of the inflation port 302 and glue seal 412 proximal of the port 302.

Thus, the catheter assembly 120 can be conveniently constructed by inserting catheter 130 into the aperture 334 and channel 380 of the hub housing 330, and subsequently injecting glue into glue holes (400, 402). Glue seals (410, 412) both help to retain catheter 130 in hub 140 and prevent the escape of pressurized fluid when it is supplied via the inflation port 302. Specifically, distal glue seal 410 prevents escape of pressurized fluid from the distal end of housing 300, and proximal glue seal 412 prevents the escape of pressurized fluid into channel 382 at the proximal portion 142 of hub 140.

FIGS. 6B and 6C show cross-sections of hub 140 taken along lines A-A and B-B in FIG. 6A. FIG. 6B shows a view from the location of proximal glue holes 402, where glue seal 412 has formed around catheter 130. FIG. 6C shows a view from the location where the outer lumen 390 of catheter 130 itself is sealed. Here, seal 416 prevents the escape of pressurized fluid from outer lumen 390 through the proximal tip of catheter 130 and into channel 380.

The delivery port 304 is in fluid communication with the channel 382 of hub housing 300 and inner lumen 392 of catheter 130. As a result, various diagnostic and/or therapeutic agents may be delivered into the inner lumen 392 and to the distal end of catheter 130. Such agents can be delivered directly to the target site, and can be supplied through the delivery port 304 continuous, periodic, and/or timed release.

As explained above, housing 300 also includes an aperture 350 at the proximal end thereof, and in certain advantageous embodiments, an imaging device 180 is inserted therein. When sealing member 252 is compressed by a driver 358, it expands inwardly toward the center of the aperture 350, resulting in a tightening around imaging device 180. As the components enter a fully closed position, imaging device is securely fixed in place by the compressed plug 252, which also creates a seal around it. By reversing this process, the seal can be loosened so that the imaging device may be moved, and then tightened again.

The imaging device 180 can be advanced out the distal end of catheter 130, allowing a user to shine light on the target site and view the reflected light from the body cavity. However, moving the imaging device 180 out of the catheter can cause it to become covered with biological material, which obstructs the practitioner's view. In order to remedy this problem, the distal portion of 134 of catheter 130 includes a cleaning element 138, as shown in FIGS. 2A-B.

Figure 3B:
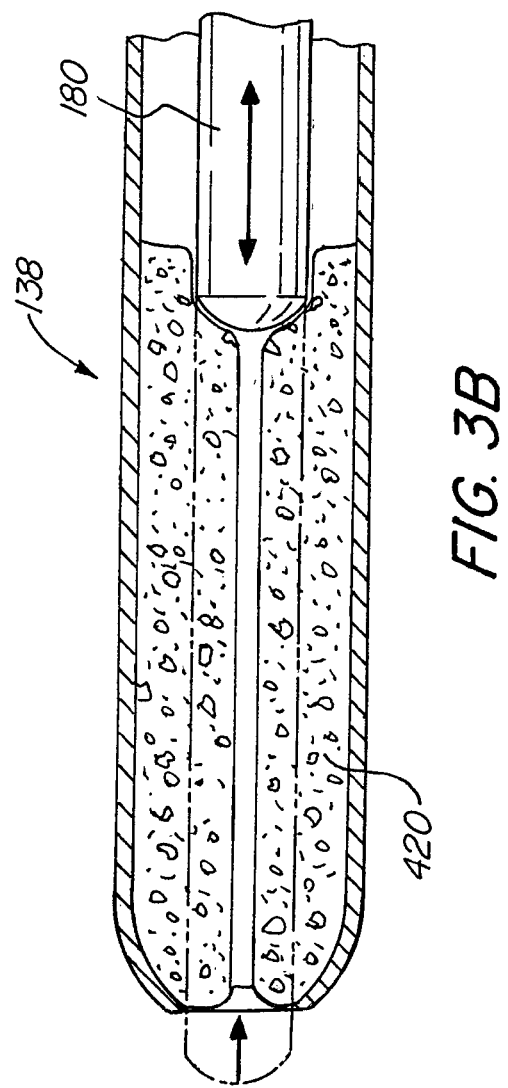

As illustrated in FIG. 3B, the cleaning 138 element may, for example, comprise a porous material 420, charged with a cleaning solution. As another example, the cleaning member 138 may comprise a series of flexing flaps 422 with spacers 424 separating them. Any suitable cleaning member 138 may be employed, such as those described in U.S. Published Patent Application No. 2012/0238816 by Gunday et al., the specification of which is hereby incorporated herein in its entirety. The imaging device 180 can be partially retracted into catheter 130 such that the lens or other optical element at the end of the device can be pushed through the cleaning element 138 to wipe all materials from the surface of the device. This allows a medical practitioner to clean the tip of the imaging device 180 during a procedure by retracting and re-advancing the distal tip of the imaging device 180 so that the operator can then continue the procedure with a clear view. This action can be periodically performed during a surgery as necessary to maintain a clear view.

The inner lumen 392 of catheter 130 can be used to deliver any number of things to assist with opening the cavity, circulation, aspiration, respiration, assisting the decomposition of an obstruction, or stimulating healing in the affected area, including air, aspirates, drugs, biologics, biogenetic agents, nano-particulates, solutions, stem cell and gene therapies, and stents and scaffolds. Specifically, the device could be used for the deployment and implantation of pro-generative vehicles and/or catalysts in the repair, treatment, and therapy of the targeted areas, including biologic, nano-particulate materials and/or biogenetic materials, structures, scaffolds, and similar devices and vehicles, including, for example, bone morphogenetic proteins, microcrystalline nano-particulates, collagens, de-mineralized bone chips, calcium based structures, poly glycolic acids, poly lactic acids, and hyaluronic acids. The device can likewise be used for the deployment and implantation of inert, inelastic, and semi-rigid materials, such as, for example, PEEK, ceramic, cobalt chrome, titanium, and stainless steel, and for the implantation of reinforcing constructs within, along, and/or around anatomic structures, which may be deployed and then impregnated, impacted, and otherwise filled, either prior to or after insertion, with inert materials including, for example, polymethyl methacrylate, bone cements, polyethylene, polypropylene, latex, and PEEK.

Figure 7C:
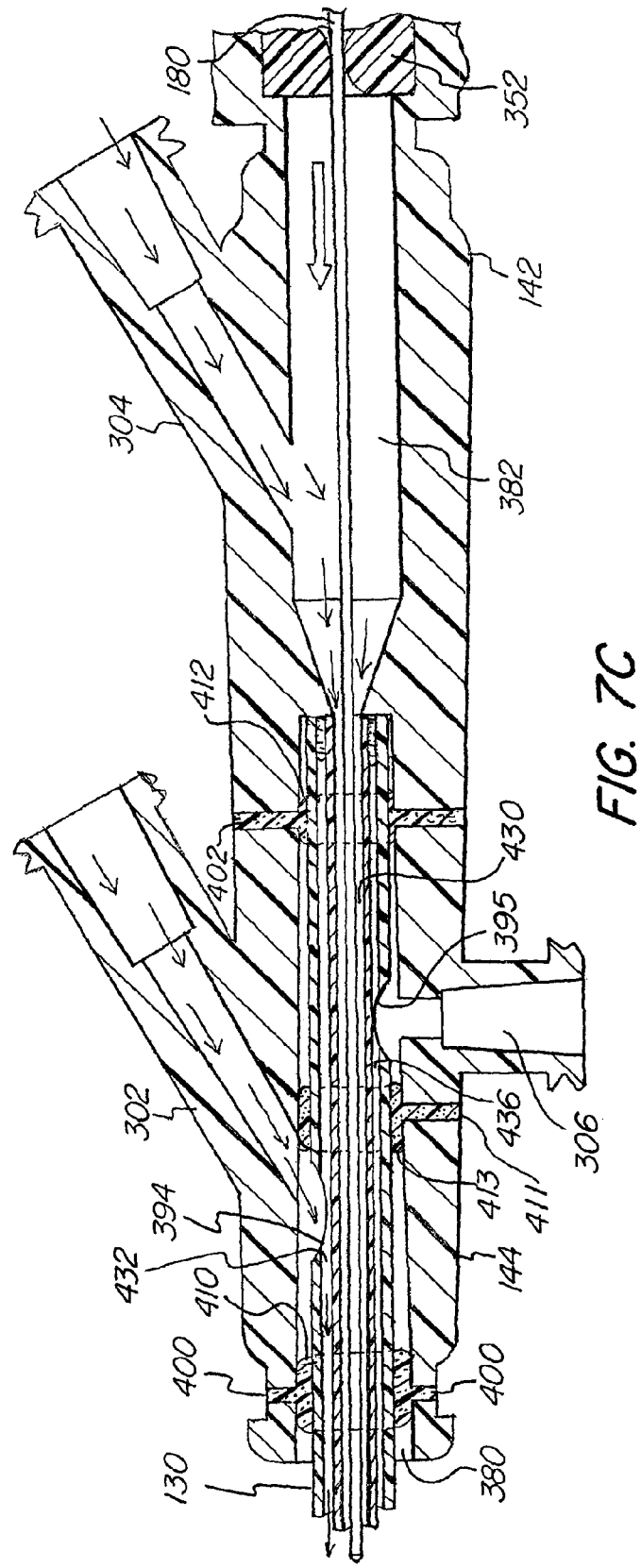
FIG. 7C is cross-sectional plan view of the hub of FIG. 7A.

As shown in FIGS. 7A-B, in certain advantageous embodiments, the catheter 130 has a dual inflation lumen structure instead of outer lumen 390 and the housing 300 includes a second inflation port 306. Referring to FIGS. 7B-C, fluid supplied into aperture 394 enters lumen 432 of the catheter 130. The wall of the proximal portion of the catheter 130 also includes another aperture 395, through which fluid is introduced into lumen 436. Additional glue holes 411 are provided for injecting glue between the catheter 130 and the wall of the hub channel 380 to create another seal 413, such the fluid supplied by ports 302 and 306 are isolated to lumen 432 and 436, respectively.

Figure 7D:
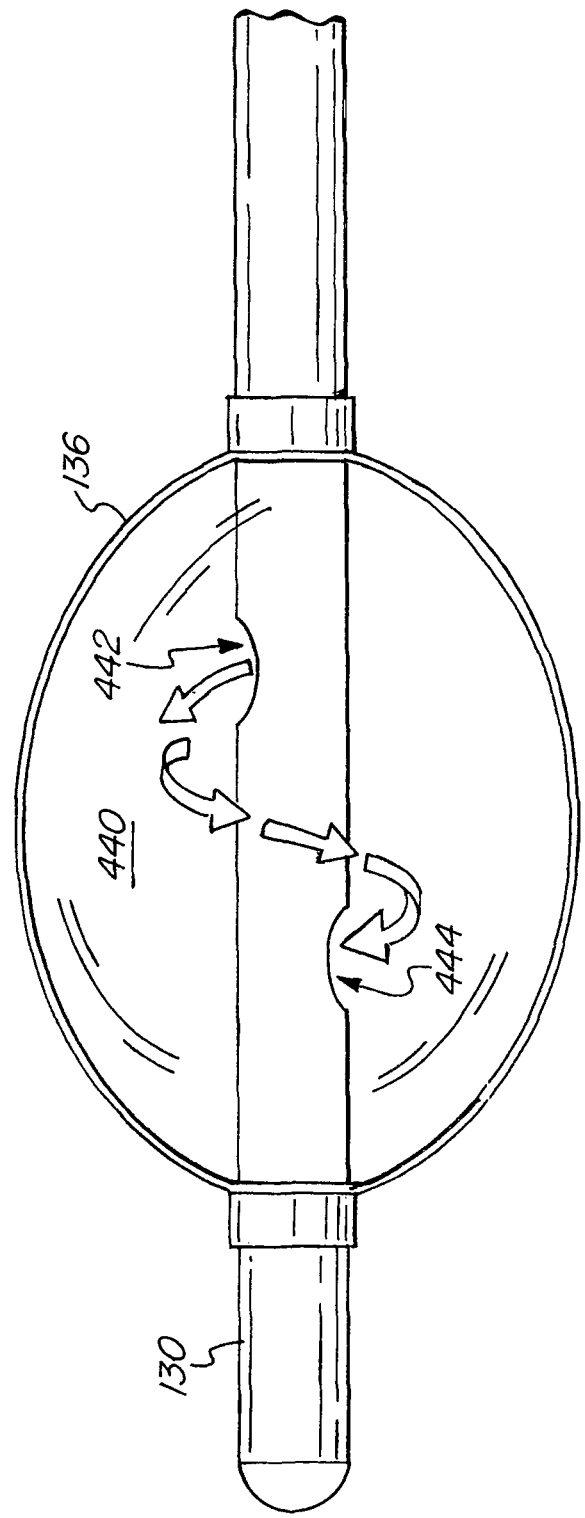
FIG. 7D is an isometric view of the distal portion of the balloon catheter of FIG. 7B.

As shown in FIGS. 7C-D, lumen 432 delivers fluid through aperture 442 in the wall of the distal portion of the catheter 130 and into the inflation chamber 440 of the balloon 136. Similarly, lumen 436 is in fluid communication with the inflation chamber 440 of balloon 136 via another aperture 444 in the wall of the distal portion of the catheter 130. This dual lumen structure is particular useful for various purposes.

In cases where the fluid being delivered to the inflation chamber 440 is a gas, such as air, both port 302 and port 306 can be used to supply the air simultaneously. This results in a significant increase of the cross sectional area, which increases the flow rate, while keeping the overall outer diameter of the catheter 130 as small as possible. Additionally, the additional port 306 can be used to flush air out of the system, which can be accomplished by introducing a liquid into the inflation port 302 and lumen 432 until the liquid begins to discharge from the additional inflation port 306. The additional inflation port can then be sealed with a cap 308, resulting in a system that is fully purged of air.

When the fluid being supplied is a liquid, such as water, and there is no need to maintain significant pressure within the system, the additional port 306 can remain open, such that the liquid can be circulated through the system, through lumen 432 and aperture 442, into the inflation chamber 440, back through aperture 444 and lumen 436, and out port 306. This can be particularly useful in applications where the temperature of the liquid in the balloon must be maintained, such as in bronchial thermoplasty, where it is desirable to heat the tissue. In order to accomplish this, heated water can be continuously delivered to the balloon 136 to heat the tissue. A fluid source can continuously supply new heated water to the balloon, or the water continuously being discharged from the port 306 can be run through a heating device and ultimately recirculated back into port 302.

The catheter also includes a lumen 430 for accommodating an imaging device 180 and agents delivered via delivery port 304, as previously described.

Figure 11:
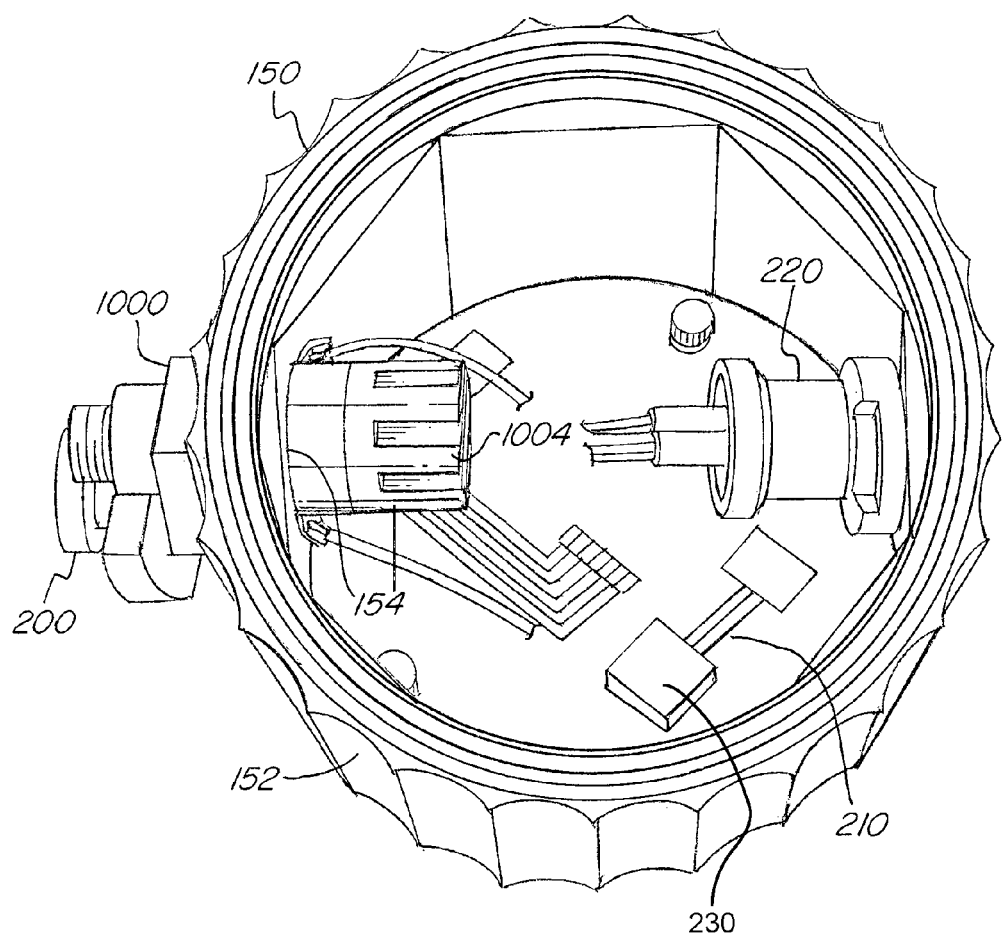
FIG. 11 is an isometric top view of the imaging module of FIG. 1.

Returning to FIG. 1, the imaging device 180 incorporates a light guide 190 and image guide 200. Because the body interior must be illuminated in order to obtain images, light source 1000 provides light to imaging device 180 via light guide 190. This light travels through imaging device 180 and out the distal end thereof, where it reflects off the target site inside the patient's body. The reflected light travels back through the imaging device 180 to the imaging module 150 via image guide 200. Referring to FIG. 11, this optical signal is then processed by image circuitry 210 and output via USB port 220.

Figure 8:
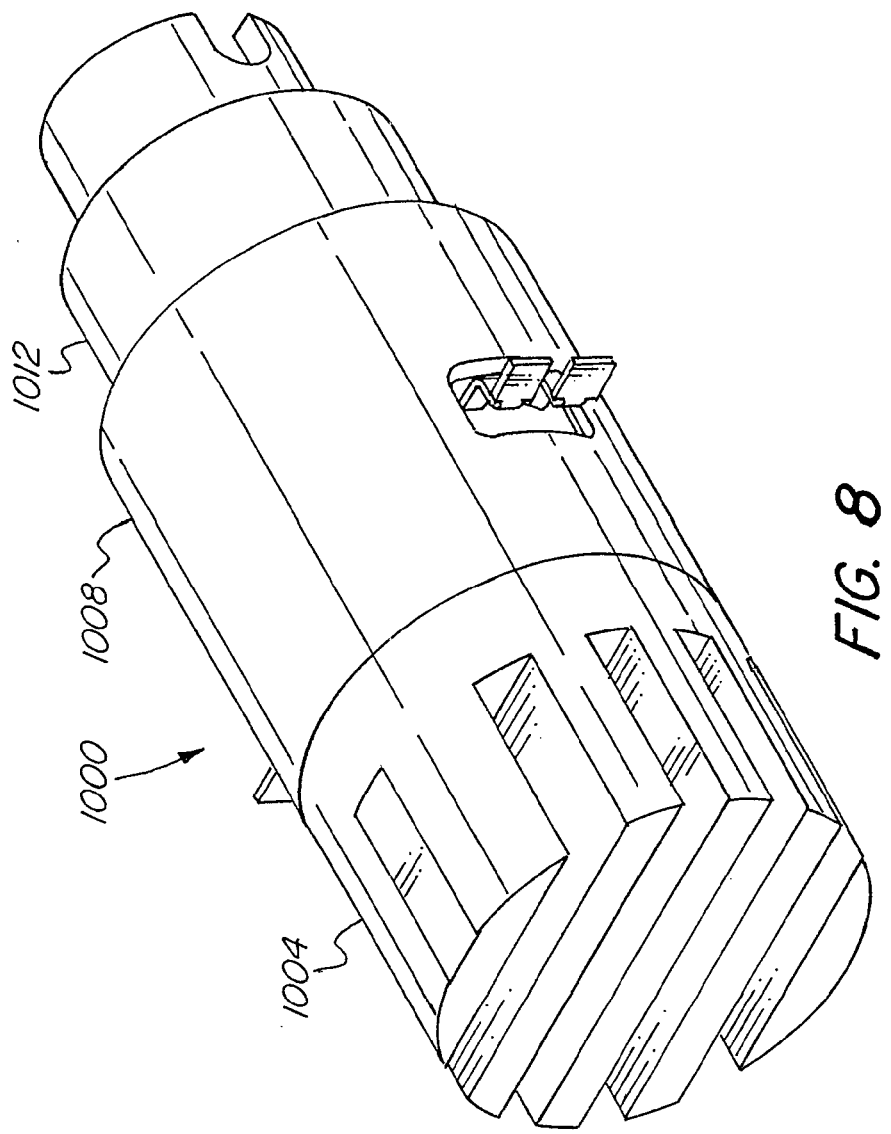
FIG. 8 is an isometric view of the light source of the catheter assembly of FIG. 1.
Figure 9:
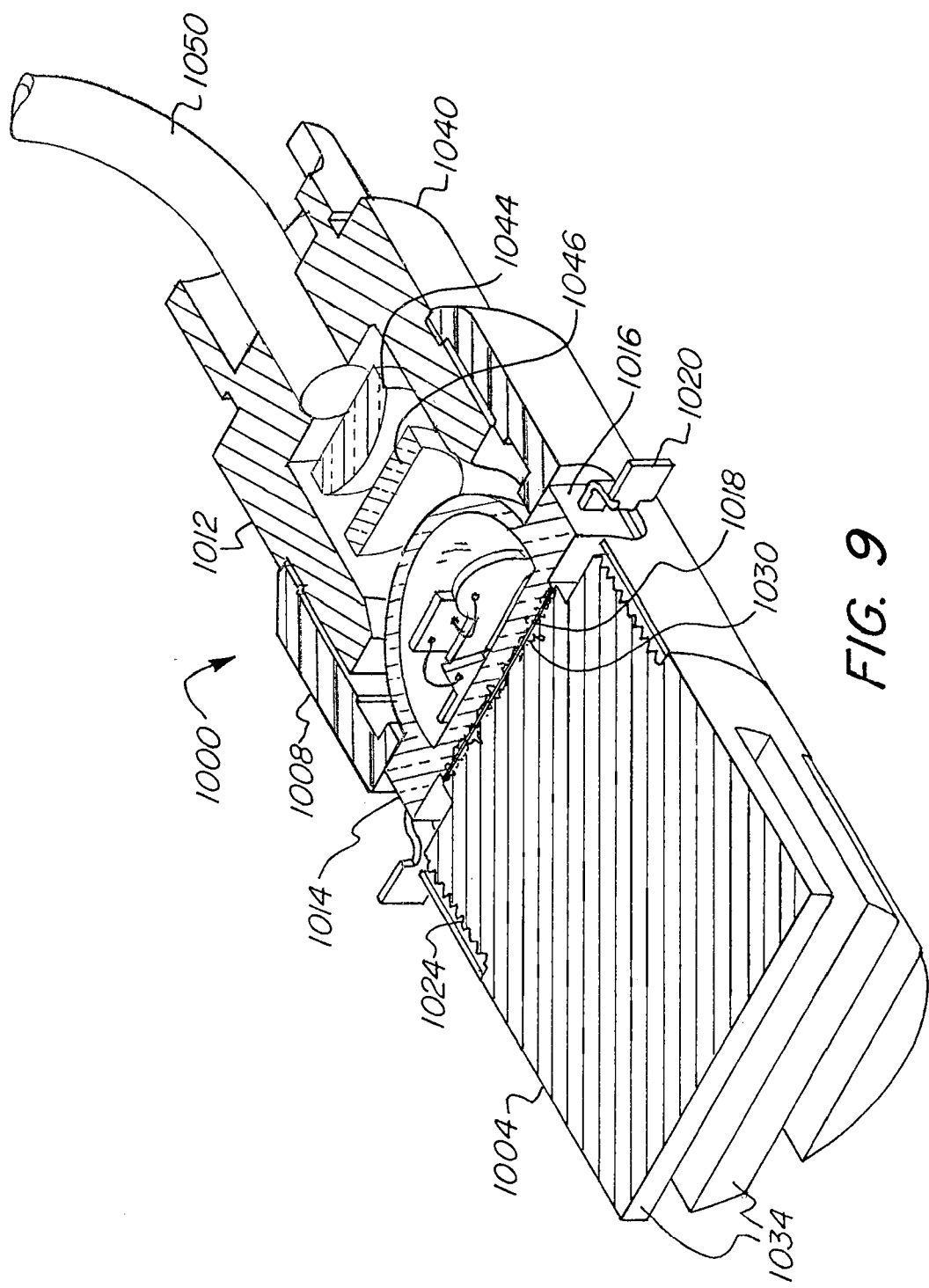
FIG. 9 is cross-sectional isometric view of the light source of FIG. 8.

FIGS. 8-9 illustrate one exemplary embodiment of the light source 1000. Light source 1000 comprises a heat sink 1004, an insulation housing 1008, and a collimator 1012. A light emitting diode (LED) 1014 for generating light is disposed within insulation housing 1008. The LED 1014 includes a housing 1016 and surface 1018, and electrical leads 1020 control and power the LED 1014.

Figure 10:
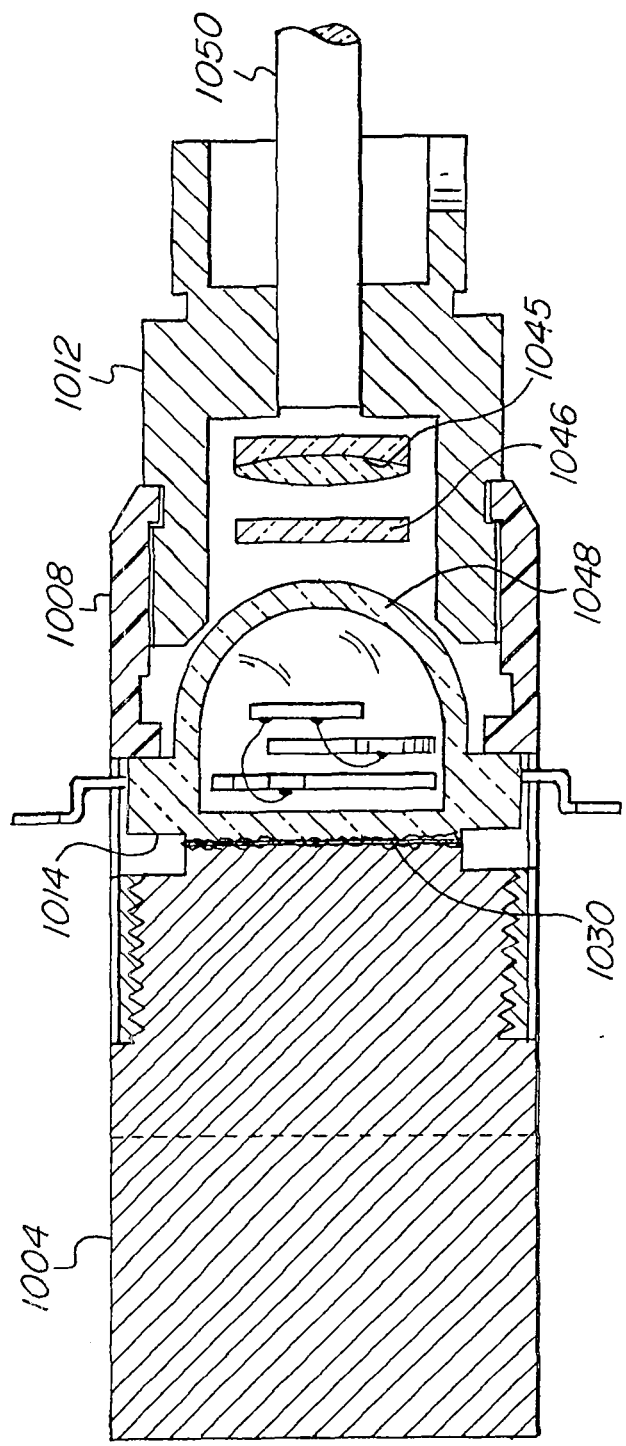
FIG. 10 is a cross-sectional view of the light source of FIG. 8.

As shown in FIGS. 9 and 10, both heat sink 1004 and housing 1008 are threaded, such that heat sink 1004 is coupled to housing 1008 via threads 1024. Heat sink 1004 can be screwed into housing 1008 until it abuts surface 1018 of LED 1014. It should also be noted that other, non-threaded coupling mechanisms may be employed for coupling the heat sink to 1004 to the housing 1008.

Surface 1018 is a generally flat surface made of a thermally conductive material, such as steel or aluminum, which provides a good interface for heat sink 1004. Surface 1018 is sufficiently conductive, and has sufficient surface area, to transfer significant heat from LED 1014 to heat sink 1004.

A thermal compound 1030 is sandwiched between surface 1018 and heat sink 1004. Thermal compound 1030 improves thermal conductance between LED 1014 and heat sink 1004. The medium of thermal compound is typically silicone grease. However, other appropriate substances may be used, such as mineral oil. The thermal compound may comprises any of various thermally conductive substances, including ceramic powders, such as beryllium oxide, aluminum nitride, aluminum oxide, zinc oxide, or silicon dioxide, metal conductors, such as silver or aluminum, carbon-based conductors, such as diamond powder or short carbon fibers, and liquid metals, such as gallium alloys. Alternatively, a phase change metal alloy can be used.

The thermal compound 1030, which has much better conductivity than air, improves the thermal conductivity of the interface between surface 1018 and heat sink 1004 by filling microscopic air gaps resulting from the imperfect nature of those surfaces. This use of a thermally conductive surface 1018 together with a thermal compound 1030 facilitates a very efficient transfer of heat generated by LED 1014 to heat sink 1004.

Meanwhile, insulation housing 1008 is made of a material of very low thermal conductance, thereby acting as an insulator to prevent the heat generated by LED 1014 from radiating outwardly from the light source 1000 in a radial direction. In advantageous embodiments, this insulation housing 1008 comprises polyimide. As a result, the area radially surrounding light source 1000, which may be a handheld device to which light source 1000 is mounted, as further explained below, is insulated from the heat produced by the LED 1014, which is instead channeled back into heat sink 1004 via surface 1018 and thermal compound 1030.

Heat sink 1004 comprises fins 1034 to improve the thermal conductance of heat sink 1004 with the ambient environment. Fins 1034 increase the surface area of the exterior of heat sink 1004, thereby increasing the contact area between the atmosphere and heat sink 1004. This improves the efficiency of heat sink 1004 by increasing the size of the interface between heat sink 1004 and the medium into which heat sink 1004 is dissipating the heat, thereby increasing the amount of heat that heat sink 1004 can channel from LED 1014 and emit into the environment. Heat sink 1004 may be made of a highly thermally conductive material, such as aluminum.

Collimator 1012, which is also coupled to housing 1008, includes an optics housing 1040 and collimating optics 1044. Collimator 1012 receives the light emitted from LED 1014 at one end, and at the other end, accommodates the distal end of a light guide 1050. The collimating optics 1044 narrow the light received from LED 1014 to focus it on the input of light guide 1050. This narrowing of the light may involve approximately collimating, or rendering parallel, the light rays, or reducing the cross-sectional area of the light beam, or both.

In order to accomplish this, the collimator 1012 may include one or more optical elements, including a positive lens for converging the light rays, such as plano-convex lens 1044 or a doublet 1045. This may be an aspheric lens 1044. Additionally, the LED housing 1016 itself may comprise an optical element 1048 for converging the light rays, such as a condenser lens. In addition, the interior of the collimator that accommodates collimating optics 1044 may have a reduced cross-section or an aperture stop to narrow the light beam. Additionally, a filter 1046, for filtering certain wavelengths of light, such as heat generating infrared light, may be disposed between LED 1014 and collimating optics 1044.

LED 1014 is powered and controlled via electrical leads 330. The brightness of LED 1014 can be controlled by varying the voltage supplied to leads 330. The brightness of LED 1014 can also be pulse-width modulated via leads 330, so that LED 1014 can be on for varying duty cycles, and the longer the duty cycle that LED 1014 is on, the more light it will output over time and the brighter LED 1014 will be.

As shown in FIG. 11, imaging module 150 has a wall 152 with a hole 154 passing therethrough. Light source 1000 is mounted to wall 152 such that housing 1008 is partially disposed in the hole 154 and heat sink 1004 is disposed in the interior of imaging module 150. As a result, the insulation housing 1008 insulates the wall 152 from the heat generated by LED 1014, thereby preventing undesirable heating of the imaging module 150. This not only prevents injury to people using or touching the medical device 110, but it also prevents damage to other sensitive equipment in the device, such as the image guide 200 that is also mounted to the device.

Preventing inadvertent burns is not only important for avoiding injury to the medical practitioner using the device, but is extremely important for the patient, even if the patient is not directly in contact with the device, because it prevents shock and sudden uncontrolled reflexive movement of the practitioner, which would injure the patient during many types of delicate surgical procedures. Further, it prevents injury to patients who may be unconscious during a procedure and unable to move their bodies to avoid prolonged exposure to overheated parts.

Image guide 200 is optically coupled to image circuitry 210. Image circuitry 210 comprises a charge-coupled device (CCD) matrix (230), floating gate transistor matrix (230), or other means to convert images into digital or analog electrical information. Thus, image circuitry 210 produces an electrical representation of the optical signal (i.e. images) supplied by image guide 200, and comprises circuitry that facilitates the transfer of electrical image data to a computer.

For example, as shown in FIG. 11, image circuitry 210 includes a universal serial bus (USB) port 220 and necessary adaptation circuitry. In some embodiments, image circuitry 210 does little or no image processing to the data and merely converts the optical images to electrical data and transfers it to a computer. In those embodiments, the computer performs the image processing to produce a video feed or still images that are suitable for recording the procedure and/or providing the operator a live image feed of the site of the procedure within the patient's body.

It should be understood that the foregoing is illustrative and not limiting, and that obvious modifications may be made by those skilled in the art without departing from the spirit of the invention. Although the invention has been described with reference to embodiments herein, those embodiments do not limit the scope of the invention. Accordingly, reference should be made primarily to the accompanying claims, rather than the foregoing specification, to determine the scope of the invention.

What is claimed is:

1. A resector balloon system, comprising:
a handheld pump;
a hub mounted to said handheld pump;
a catheter with a proximal portion and a distal portion, wherein the proximal portion of said catheter is coupled to said hub; and
at least one balloon at the distal portion of said catheter, said balloon at least partially enclosing an inflation chamber and having a resecting surface for resecting biological material;
wherein said catheter has a first lumen in fluid communication with the inflation chamber of said balloon for supplying fluid thereto;
wherein said hub has an inflation port in fluid communication with the first lumen of said catheter for supplying fluid thereto;
wherein said catheter has a second lumen;
wherein said hub has a delivery port in fluid communication with said second lumen for delivering a therapeutic and/or diagnostic agent to the distal portion of said catheter, wherein the delivery port is also in fluid communication with a source of the therapeutic and/or diagnostic agent; and
wherein said handheld pump is in fluid communication with said inflation port such that the supply of fluid by said pump in pulsed fashion repeatedly inflates and deflates said balloon such that the resecting surface resects the biological material.

2. A resector balloon system, comprising:
a handheld pump;
a hub mounted to said handheld pump;
a catheter with a proximal portion and a distal portion, wherein the proximal portion of said catheter is coupled to said hub; and
at least one balloon at the distal portion of said catheter, said balloon at least partially enclosing an inflation chamber and having a resecting surface for resecting biological material;
wherein said catheter has a first lumen in fluid communication with the inflation chamber of said balloon for supplying fluid thereto;
wherein said hub has an inflation port in fluid communication with the first lumen of said catheter for supplying fluid thereto;
wherein said catheter has a second lumen;
wherein said hub has a delivery port in fluid communication with said second lumen for delivering an agent to the distal portion of said catheter; and
wherein said handheld pump is in fluid communication with said inflation port such that the supply of fluid by said pump in pulsed fashion repeatedly inflates and deflates said balloon such that the resecting surface resects the biological material;
wherein said hub has an aperture for inserting a device into said second lumen, further comprising an imaging device at least partially disposed in the aperture of said hub and the second lumen of said catheter.

3. The resector balloon system of claim 2, further comprising a sealing member that seals the aperture when said imaging device is disposed therein.

4. The resector balloon system of claim 1, wherein said hub comprises a housing coupled to said catheter, and said inflation port and said delivery port are integrally formed with said housing.

5. The resector balloon system of claim 1, wherein said catheter has a third lumen in fluid communication with the inflation chamber of said balloon, and wherein said hub has an additional port in fluid communication with said third lumen.

6. The resector balloon system of claim 1, wherein said hub comprises a protuberance for mounting said hub to said handheld pump.

7. The resector balloon system of claim 6, wherein the protuberance includes an indicator corresponding to at least one characteristic of said catheter and/or balloon.

8. The resector balloon system of claim 7, wherein the indicator comprises an RFID tag.

9. The resector balloon system of claim 7, wherein the indicator comprises a laser bar code.

10. The resector balloon system of claim 1, further comprising a band affixed to said hub with an indicator corresponding to at least one characteristic of said catheter and/or balloon.

11. The resector balloon system of claim 1, further comprising a strain relief mounted to a distal end of said hub around the proximal portion of said catheter.

12. The resector balloon system of claim 1, further comprising a cleaning member at the distal portion of said catheter for cleaning the imaging device, wherein said cleaning member includes a flexible material at least partially occluding the second lumen such that the imaging device displaces at least some of the flexible material when moved therethrough.

13. The resector balloon system of claim 12, wherein said cleaning member comprises a plurality of flexing flaps at least partially occluding said conduit.

14. The resector balloon system of claim 1, wherein said catheter includes gradation marks for indicating the distance said catheter is advanced into a bodily cavity.

15. The resector balloon system of claim 1, wherein said catheter includes at least one imaging marker.

16. The resector balloon system of claim 15, wherein said at least one imaging marker includes a plurality of radio-opaque rings.

17. The resector balloon system of claim 1, wherein the resecting surface comprises a mesh on the outer surface of the balloon.

18. The resector balloon system of claim 17, wherein the mesh comprises elastane.

19. The resector balloon system of claim 1, wherein the fluid is a gas.

20. A resector balloon system, comprising:
a handheld pump adapted to be supported and operated by a user's single hand;
a hub mounted to said handheld pump;
a catheter with a proximal portion and a distal portion, wherein the proximal portion of said catheter is coupled to said hub; and
at least one resector balloon at the distal portion of said catheter for resecting biological material;
an imaging module coupled to and abutting said handheld pump; and
an imaging device coupled to said imaging module and at least partially disposed in said catheter.

21. The resector balloon system of claim 20, wherein:
said imaging device comprises an image guide for transmitting an optical signal; and
said imaging module comprises image circuitry optically coupled to said imaging device that converts the optical signal to electrical data.

22. The resector balloon system of claim 21, wherein said image circuitry comprises a charge-coupled device matrix.

23. The resector balloon system of claim 21, wherein said image circuitry comprises a floating gate transistor matrix.

24. The resector balloon system of claim 21, wherein said image circuitry outputs the electrical data via a universal serial bus port.

25. The resector balloon system of claim 21, wherein:
said imaging device further comprises a light guide for transmitting light; and
said imaging module further comprises a light source for supplying light to the light guide.

26. The resector balloon system of claim 25, wherein said light source comprises:
an LED for supplying light, said LED having a surface that conducts heat generated by said LED;
an optical element that receives and transmits the light supplied by said LED;
an insulation housing in which said LED is disposed for insulating the LED;
a heat sink coupled to said insulation housing and having a surface adjacent to the surface of said LED that conducts heat; and
a thermal compound disposed between the surface of said heat sink and the surface of said LED that conducts heat.

27. The resector balloon system of claim 26, wherein said insulation housing comprises polyimide.

28. The resector balloon system of claim 26, wherein said light source further comprises a collimator coupled to said insulation housing, wherein said optical element is disposed in said collimator.

29. The resector balloon system of claim 20, wherein said hub has an aperture and wherein said imaging device is disposed in the aperture.

* * * * *